United States Patent [19]

Henderson

[11] Patent Number: 4,534,827
[45] Date of Patent: Aug. 13, 1985

[54] CUTTING IMPLEMENT AND METHOD OF MAKING SAME

[76] Inventor: Donald W. Henderson, 20 Woodlane Rd., Ithaca, N.Y. 14850

[21] Appl. No.: 527,165

[22] Filed: Aug. 26, 1983

[51] Int. Cl.³ .............. C23F 1/00; C23F 1/06; A61B 17/32
[52] U.S. Cl. .................. 156/647; 156/667; 252/79.2; 128/305; 30/346
[58] Field of Search ............ 156/625, 647, 654, 667; 30/346, 350, 346.53, 346.54; 29/576 T; 128/305; 423/625; 252/79.2

[56] References Cited

U.S. PATENT DOCUMENTS

| | | | |
|---|---|---|---|
| 3,636,955 | 1/1972 | Kurtz | 128/305 |
| 3,753,775 | 8/1973 | Robinson et al. | 156/646 X |
| 3,894,337 | 7/1975 | Jones | 30/346.54 |
| 3,964,942 | 6/1976 | Berkenblit et al. | 156/647 X |
| 4,124,698 | 11/1978 | Hemmat et al. | 156/647 X |

OTHER PUBLICATIONS

Reisman et al., "The Chemical Polishing of Sapphire and MgAL Spinel", Journal of the Electrochemical Society, vol. 118, No. 10, Oct. (1971).

Primary Examiner—Edward C. Kimlin
Assistant Examiner—Ramon R. Hoch
Attorney, Agent, or Firm—Weingarten, Schurgin Gagnebin & Hayes

[57] ABSTRACT

A cutting tool, preferably in the form of a scalpel, microtome or razor blade is fabricated from single crystal material such as aluminum oxide with a preferential etching process to produce a radius of curvature less than 100 Angstroms on the edge. Depending upon the etchant, the crystallographic orientation of the blank and the resulting different etch rates on blade surfaces, the preferential etching process not only sharpens a preformed edge but also, in one embodiment, produces an opposing edge which meets the sharpened edge at a point, thereby to produce a particularly efficient scalpel blade configuration having two cutting edges converging at a point for plunging and cutting. With respect to the sharpening of the cutting edge, consistent with all other blade forming requirements, the subject blade is made to a maximum sharpness by utilizing a maximum ratio of bevel plane etch rate to edge plane etch rate. This maximum ratio maximizes the edge sharpness when a steady state etching geometry has been achieved. In one embodiment, and for a given edge sharpness, blade drag is minimized by selecting the crystallographic orientation and etchant such that the etchant chemically polishes the bevels and maintains the planarity of the bevel planes. In order to achieve identical etching of the bevels meeting at the blade edge and thus maintain original blade geometry, the blank can be oriented such that the edge forming planes are crystallographically identical planes.

8 Claims, 9 Drawing Figures

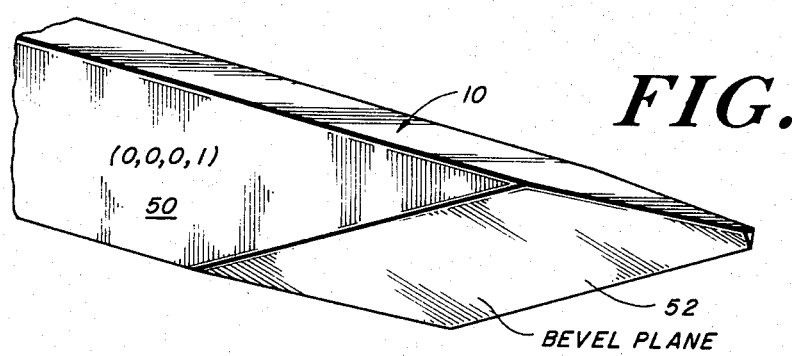
FIG. 5
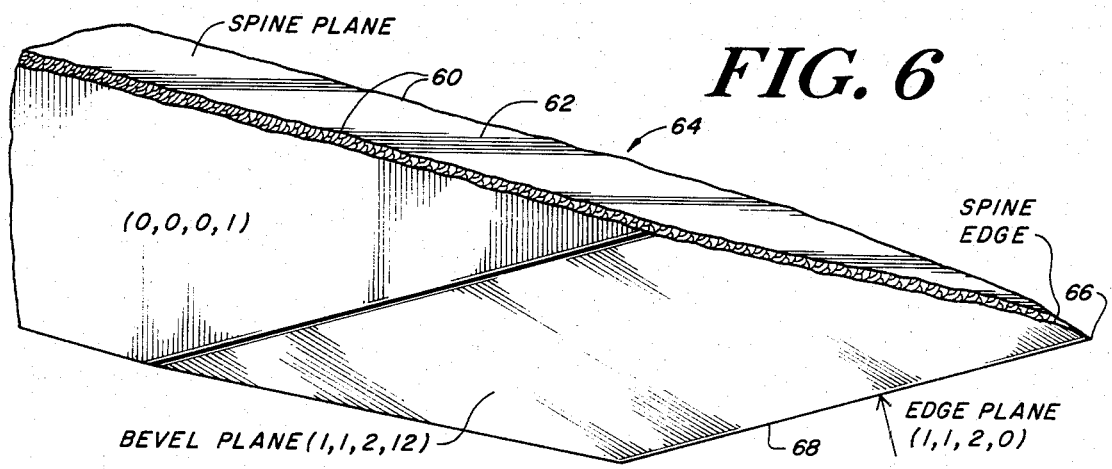
FIG. 6
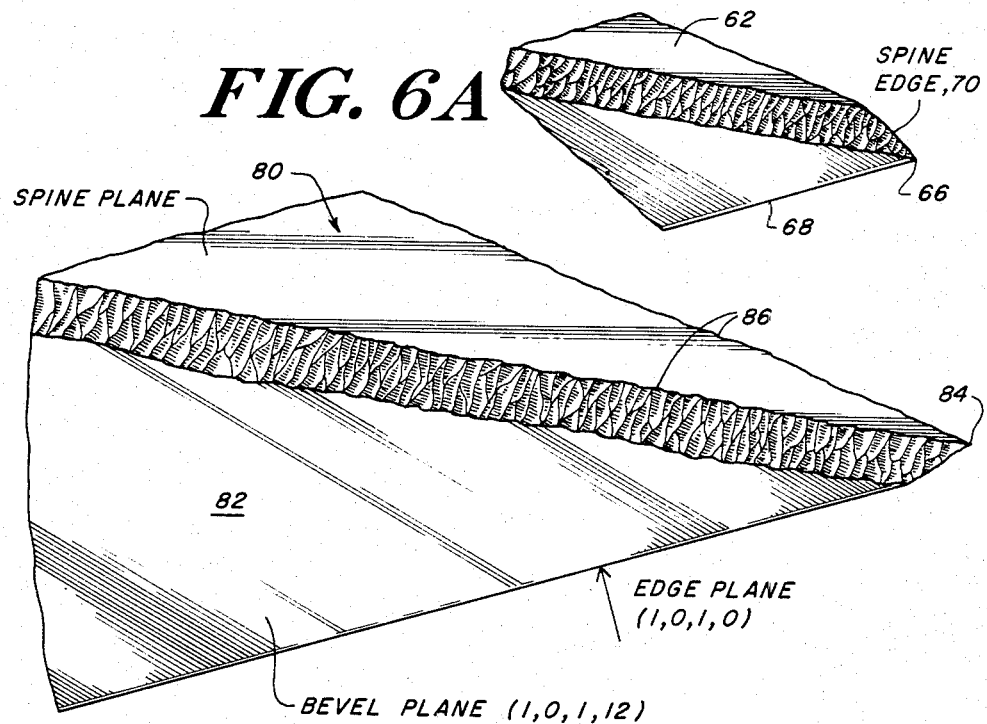
FIG. 6A
FIG. 7

CUTTING IMPLEMENT AND METHOD OF MAKING SAME

FIELD OF INVENTION

This invention relates to cutting implements made of single crystal materials and more particularly to cutting instruments and the methods of manufacture, the blades having exceptional sharpness, minimal blade drag, and exceptionally high wear resistance.

BACKGROUND OF THE INVENTION

While the subject invention will be described in connection with the manufacture of exceptionally sharp scalpels, it will be appreciated that the invention discussed herein relates to any cutting implement, the sharpness of which and the durability of which is of importance. As such, the cutting implements described herein include microtomes, razor blades, and knives as well as surgical scalpels.

The best blades produced by current metallic technology have an edge radius of curvature of approximately 500 Angstroms. Diamond blades have been produced which have an edge radius of curvature of approximately 400 Angstroms. More recently, ruby blades have been produced with an edge radius of curvature of 350 Angstroms. All of the above blades have been produced by conventional lapping procedures.

While U.S. Pat. Nos. 2,070,281; 2,838,049; 2,898,906; 3,636,955; 3,844,272; and 3,945,117 describe a number of surgical instruments involving cutting edges or puncturing tools, their manufacture by the techniques described therein produce instruments whose wear characteristics, sharpness and blade drag present problems to surgeons and those other personnel who employ them. In this context the term blade drag refers to the force which resists the movement of the blade in a cutting procedure. The amount of tissue damage during surgery is directly dependent upon the sharpness of the blade and other factors contributing to blade drag, with the amount of extraneous tissue damage determining healing time, as well as the extent of scarring which can accompany the surgical operation.

More particularly, with respect to radial keratotomy which is a procedure in which radial cuts are made about the periphery of the cornea, it is imperative that the cuts made have smooth and flat side walls to reduce the amount of refraction and scattering caused by uneven side walls. Scalpels and other cutting instruments to date, either because of blade drag or because of a lack of sharpness, produce ragged side walls at least to the extent that after surgery, patients experience a diffuse glare looking into a strong light. The ability to provide a scalpel which can produce smooth, flat side walls during such a procedure is therefore of paramount importance.

With respect to microtome applications it will be appreciated that the microtome is an instrument which provides slices of tissue embedded in a carrier. It is of paramount importance especially in electron microscopy to produce microtome samples as thin as possible. In both electron microscopy and optical microscopy, it is of importance that the distortions in the sample due to cutting be minimized, with the distortions again being a function of blade sharpness and other factors contributing to blade drag. The minimum thickness of a substantially undistorted slice is of course directly a function of blade sharpness.

With respect to scalpels and other cutting instruments made of metal, with current technology the wear characteristics are such that the blades dull significantly during use and, more particularly, during a single surgical operation. When delicate surgery is required, the ability to maintain a constant sharpness cutting edge is important to the success of the delicate surgery, with the sharper the cutting edge the better.

It will be appreciated that aluminum oxide, ruby and sapphire are all closely related materials and vary only in the concentrations of dopant metal oxides. All of these materials have the same crystal structure and as such show great simularity in physical behavior. For the purposes of this invention these materials will be referred to as aluminum oxide.

It should be pointed out that in the past, aluminum oxide blades have been utilized for surgical instruments. These blades of sapphire or ruby have in the past been made by lapping techniques which in general produce blades whose drag characteristics and sharpness, while exceeding that associated with metallic blades, nonetheless are nonoptimal for the applications described above. In addition, it will be appreciated that, in all lapping procedures, material is removed from the blade edge mechanically through abrasion, which leaves near-surface damage in the region of the bevel and edge which increases the propensity for wear and fracture.

While not used for single crystalline blades, preferential etching techniques have in the past been utilized in the semiconductor industry for the etching of aluminum oxide and silicon. Chemical polishing in the form of etching has also been utilized in material science in a wide spectrum of applications other than for the production of extremely sharp edges for cutting implements made from single crystal material.

An exception to the above is described in U.S. Pat. No. 4,124,698 in which monocrystalline ribbon produced by a so-called "EFG" process through the utilization of a die is provided with sharpened edges through the utilization of a solvent in the form of a melt of vanadium pentoxide or potassium tantilate niobate by moving a blank of the ribbon through a melt or body of solvent in a direction generally normal to the plane of the ribbon. As mentioned in this patent, the degree of edge uniformity is dependent upon the movement of the ribbon through the solvent to achieve laminar flow, with laminar flow depending upon many process variables, including the shape of the ribbon, the crucible utilized and the viscosity of the solvent. As described in this patent, unidirectional movement oftentimes results in dissolving away portions of the ribbon along only one side. It is said that it is generally preferable to reciprocate the ribbon in the solvent in order to provide for the required edge.

In this patent it is preferred that the ribbon be of a type which has the crystallographic c-axis disposed parallel to its longitudinal geometric axis, since such ribbons exhibit the best edge sharpening when subjected to the method of sharpening described in the patent. In this patent, it will be appreciated that the c-axis lies in the plane of the blade whereas, as will be described hereinafter, in the subject method the c-axis is perpendicular to the plane of the blade and no relative movement of the blade and solvent is required or even desirable.

U.S. Pat. No. 3,894,337 describes the formation of blades, and more particularly a razor blade having a single crystal of α-aluminum oxide for the cutting edge thereof. This blade is formed by grinding or etching single crystals of aluminum oxide. The crystals are grown preferably in a shape corresponding to the desired cross section of the blade to facilitate formation of the cutting edge. However, in the above-mentioned patent no specific procedure or orientation for single crystals of α-aluminum oxide is described other than to say that it is convenient to produce cutting edges substantially parallel to the c-axis of the unit cell as opposed to perpendicular to the c-axis, which is one of the aspects of the subject invention to be described. Moreover, a number of etchants are listed in this patent which, for a variety of reasons, do not provide for pit-free chemically polished surfaces over a wide range of crystallographic orientations due to difficulty in handling, temperature processing constraints and physical limitations of the etch-material system. It will be appreciated that the selection of a particular etchant is critical with respect to chemical polishing and the prevention of pitting. It is therefore advantageous to select an etchant which polishes over a large range of crystallographic orientations for the formation of cutting tools.

It is also important to note that U.S. Pat. No. 3,894,337 omits mention of the utilization of a combination of sulfuric acid and phosphoric acid as an etchant for the production of blades. As will be discussed, the combination of these acids along with certain physical constraints is important to the subject invention.

As discussed in the *Journal of the Electrochemical Society*, October, 1971, Vol. 118, No. 10, sapphire and more recently MgAl spinnel ($MgAl_2O_4$) have been employed extensively as single crystal dielectric substrates for the epitaxial growth of a variety of materials. Wafers of these dielectrics are usually available only in mechanically polished form. Because of the damage introduced during mechanical preparation, many and varied liquid and gas phase treatments have been applied prior to use, to effect non-selective etching or chemical polishing of the surfaces. Among these are included molten borax, heated phosphoric acid, molten $V_2O_5$, molten lead fluoride, heated vaporous sulfur fluorides, heated vaporous fluorinated hydrocarbons, $HCL-H_2$ at elevated temperatures and $H_2$ annealing among others. As described in this article, none of the above-mentioned approaches has proved to be satisfactory for a variety of reasons. Molten salt approaches are cumbersome or often are somewhat selective, and in common with others noted above are highly orientation dependent. Vapor phase etchants are quite orientation dependent and sometimes exhibit low removal rates. Heated phosphoric acid is said to have shown some promise but tends to leave insoluble residues behind. Further, because it dehydrates and polymerizes, its chemical behavior is said to vary continuously with time at temperature. $H_3PO_4$ is also said to be somewhat orientation selective and frequently results in dense pitting. Annealing in $H_2$ exhibits a vanishingly low removal rate and was found not to eliminate polishing scratch damage when subjected subsequently to the liquid phase portion of the polishing technique. However, the use of a combination of $H_2SO_4$ and $H_3PO_4$ is utilized as the preferred etchant in this paper.

The content of this paper was utilized extensively in U.S. Pat. No. 3,964,942. In this patent the polishing of single crystal dielectrics is described utilizing a mixture of sulfuric and phosphoric acid in which polishing is achieved for sapphire having certain crystallographic orientations not optimal to the formation of cutting instruments. It will be appreciated that nowhere in this patent is mentioned the formation of edges for cutting implements, the primary purpose of the patent being directed to the formation of crystal wafers of aluminum oxide or magnesium aluminum spinnel with damage free surfaces.

Other patents describing the etching of sapphire include U.S. Pat. No. 4,052,251 in which sapphire is etched utilizing sulphur hexafluoride. Moreover, U.S. Pat. No. 3,808,065 describes a method of polishing sapphire and spinnel utilizing molten borax. As described above there are certain problems with the utilization of molten borax as an etchant. Finally, with respect to chemically polishing, U.S. Pat. No. 3,878,005 discusses the use of lead monoxide and boric anhydride at reasonably high temperatures of 1100° C. to 1200° C. for the chemical polishing of a variety of different ceramic materials.

With respect to the etchants utilized for etching aluminum oxide, reference is made to a paper entitled "Surface Preparation of Ceramic Oxide Crystals: Work Damage and Microhardness" by Michael F. Ehman, published in the *Journal of Electrochemical Society*, September, 1974, pp. 1240–1242, in which a combination of sulfuric acid and phosphoric acid is utilized. The thrust of this article is to describe the measurement of the depth of near-surface damage for each crystal as a function of surface orientation and the type of abrasive surface preparation techniques. Moreover, in the *Journal of Material Science*, Vol. 16, 1981, pp. 1071–1080, in an article entitled "Thermochemical Dissolution of Corundum" published by A. E. Smirnov et al. of the Institute of Crystallography, U.S.S.R. Academy of Sciences, a number of etchants are described. However, none of these etchants include the utilization of a combination of sulfuric acid and phosphoric acid. In accordance with *RCA Review*, Vol. 34, December, 1973, in an article entitled "The Chemical Polishing of Sapphire and Spinnel", P. H. Robinson and R. O. Wance describe the utilization of molten borax for polishing both sapphire and spinnel substrate orientations that are used to produce (100) oriented epitaxial silicon.

In an article by W. J. Alford and D. L. Stevens, entitled "Chemical Polishing and Etching Techniques for $Al_2O_3$ Single Crystals", published in the *Journal of the American Ceramic Society*, April, 1963, an etching procedure for revealing dislocations intersecting the (0,0,0,1) plane and planes near (2,0,2,1) in ruby and in sapphire is discussed. The surfaces to be etched were prepared by mechanical polishing and subsequent flame polishing. In this article, phosphoric acid alone was utilized, which when utilized alone without sulfuric acid, does not produce a large crystallographic range of chemical polishing necessary for the production of a wide variety of cutting instruments. Moreover, when utilizing this acid alone, the properties of the acid change with time.

In summary, what can be seen from the large amount of literature cited above is that a great many etchants including sulfuric and phosphoric acids have been utilized for the chemical cleaning and polishing of substrates to be utilized in the manufacture of semiconductor products or for the documentation and measurement of dislocation densities in ceramic materials. For the two patents mentioned which utilize monocrystalline material for the formation of cutting instruments, either lapping is utilized in the formation of the edges or chemical etching procedures are described which are difficult to control and which do not utilize a combination of sulfuric acid and phosphoric acid. Moreover, neither of these two patents utilize etchants in a manner consistent with optimal orientation of the crystallographic system for that etchant.

SUMMARY OF THE INVENTION

In contradistinction to the above-mentioned methods of producing a cutting edge, in the subject technique single crystal material is utilized with an etchant, sulfuric acid-phosphoric acid mixtures, chosen because it acts as a chemical polish over a wide range of crystallographic orientations. Moreover, the blade blank is uniquely oriented such that the edge forming planes are crystallographically identical planes to maintain blade geometry. Or perhaps more importantly, it has been found that maximizing the ratio of bevel etch rate to edge etch rate produces the sharpest edges in the above systems. Additionally, crystallographic orientation is chosen to maximize edge sharpness or to produce specific point geometries. Further, since cutting tools are produced from blanks with preformed bevels, the matching of the etchant to the material and crystallographic orientation involves matching to the predetermined bevel orientation such that the bevels are chemically polished. The chemical polishing of the bevels as well as the sharpness derived from the choice of etchant produce a blade which is stronger, is more durable, has a smoother, straighter, sharper edge, has smoother edge forming bevels and produces less drag then heretofore possible with conventional technology. All of the above constants are met using aluminum oxide, the $(0,0,0,1)$ plane for the blade plane, an etchant of a sulfuric acid-phosphoric acid mixture and a variety of edge planes including planes of the type $(1,1,\bar{2},0)$ and $(1,0,\bar{1}0)$.

As described above, conventional lapping technology results in blades having an edge radius of curvature of at best 350 Angstroms, whereas in the subject technique blades having an edge radius of curvature of 100 Angstroms or less have been fabricated and tested. Viewed from the side, blades produced by conventional technology show a much rougher blade edge profile. Etched blades, as opposed to lapped blades, are stronger because they have none of the near-surface damage associated with lapping and abrasive procedures.

As will be discussed, a method is described for fabricating a cutting instrument from single crystal aluminum oxide material in which a blank of single crystal material forming the blade has an axis which demonstrates three fold rotational symmetry for the material utilized. This particular axis is perpendicular to the planes designated $(0,0,0,1)$. In one embodiment, for aluminum oxide these crystallographic planes are made parallel, by orientation of the blank, to the bisector of the angle formed by the surfaces of the blade which form the edge.

It will be appreciated that blanks utilized in the formation of a cutting instrument have at least one beveled surface and most normally have two beveled surfaces which are in opposition and which meet at an edge the plane of which is called the edge plane. While in the blank form this edge may be flat, during the etching process it becomes rounded and the edge plane thereafter is defined as that plane which is tangent to the rounding edge and which makes equal angles with the surfaces adjacent to the edge.

Another way of viewing the subject invention as mentioned above is to note that the sharpness of a cutting instrument may be maximized when utilizing a blank of single crystalline material having a bevel and an edge by selecting for a given etchant the orientation of the materials such that the ratio of the bevel plane etch rate to the edge plane etch rate is maximized. This relationship has not heretofore been recognized and results in the formation of cutting instruments having edges of less than 100 Angstrom radius.

For aluminum oxide, sapphire or ruby, all of which have the same crystallographic structure and similar compositions, it has been found that the preferred etchant is a combination of sulfuric acid and phosphoric acid for meeting the combination of requirements for blade fabrication. While such combinations have been utilized in the past in the semiconductor industry for forming damage free substrates, it is a finding of this invention that when a symmetrically double beveled blank is cut from a crystal such that, for instance in the case of aluminum oxide, the $(0,0,0,1)$ plane is parallel to the blade plane, then the above etchant will in fact produce the sharpening of the edge to very small dimensions.

It is also a finding of the subject invention that with respect aluminum oxide, sapphire and ruby, with the above variety of constraints having been met, the etchant acts not only to etch the surfaces involved but also to chemically polish the bevels which has the added benefit of producing smoother, straighter edges than previously possible. With respect to scalpels, this further reduces blade drag and extraneous tissue damage which for surgical purposes results in an instrument which produces cuts which heal quickly with minimal scarring.

It is also a finding of this invention that when observing the above-mentioned constraints, and with using the above-mentioned etchants, the opposed bevels etch at an identical rate as would be expected from a consideration of crystal symmetry. The etching at an identical rate maintains the initial geometry of the formed blank bevel.

It has also been found in analyzing the etch rates for the bevel and the edge of the particular cutting instrument that the etch rates are temperature dependent and that by control of the temperature one can maximize the ratio of the bevel etch rate to the edge etch rate and thereby maximize the sharpness of the blade. Moreover, in contradistinction to lapped blades in which the bevel angles must be kept relatively large in order to prevent edge breakup during the abrasive lapping process it has been found that when making single crystal blades the angle between the bevels may be reduced significantly thereby also reducing the radius of curvature of the edge produced by etching.

The above constraints with respect to etchant rate of bevel etching and edge etching, and initial orientation of the crystallographic planes in the blank with respect to the edge plane chosen, apply equally well to blades with a single beveled edge as well as those having bevels to either side of the edge.

Additionally, it has been found that, in the case of aluminum oxide, given a blade plane of $(0,0,0,1)$ and an edge plane of $(1,1,\bar{2},0)$ assuming an etchant of sulfuric acid and phosphoric acid, then a second edge is formed at the point between the initially formed edge and the spine of the scalpel such that its piercing qualities are enhanced. This occurs regardless of the fact that the spine for the blade is initially unbeveled. For the same type of system but with an edge plane of (1,0,1,0) and an etchant of sulfuric acid and phosphoric acid, it has been found that while two edges are not formed, it does produce a conventional scalpel configuration with a high degree of sharpness. Thus it has been found that, although there may be other critical edge plane constraints, the most critical constraint for simultaneous optimization of edge sharpness and production of desired blade geometry is that the blade plane be the (0,0,0,1) plane in the case of aluminum oxide. More generally put, for single crystal aluminum oxide material, it is important that the crystallographic axis of the material which demonstrates three fold symmetry be approximately perpendicular to the blade plane for blades having symmetrical bevels. For single-beveled blades the set of crystallographic planes which are perpendicular to the three fold axis should be parallel to the plane which bisects the angle formed by the surfaces which are adjacent to and form the edge in question. This, coupled with the maximization of the ratio of the bevel etch rate with respect to the edge plane etch rate, achieves a maximally sharp cutting implement.

Assuming that the above constraints have been met, once the steady state has been achieved, the time in which the blade is immersed in the etchant is no longer important in determining its sharpness. Thus, in the manufacture of blades the time that the blade is left in the etchant is noncritical once this steady state has been reached.

BRIEF DESCRIPTION OF THE DRAWINGS

These and other features of the subject invention will be better understood in connection with the detail description taken in conjunction with the drawings of which:

FIG. 5 is a diagrammatic illustration of a portion of a scalpel illustrating pre-etch geometry and the crystallographic orientation of the blade therefor;

FIG. 6 is a diagrammatic illustration of the blade after etching, assuming a $(1,1,\bar{2},0)$ edge plane orientation;

FIG. 6A is a diagrammatic illustration of a portion of the blade of FIG. 6 showing the point configuration;

FIG. 7 is a diagrammatic illustration of a the blade after etching assuming a $(1,0,\bar{1},0)$ edge plane orientation.

DETAILED DESCRIPTION OF THE INVENTION

In order to reproducibly create edges using an etching technique, it is necessary that the material used be homogeneous on a scale at least as fine as the thickness of the edge that is to be produced. In addition, in order to produce the sharpest edges, using an etching technique, it is neccessary to choose a material which is anisotropic with respect to the rate of removal of surface material by etching. In other words the rate of removal of surface material by etching must be dependent on which surface of the body is exposed to the etchant. If the edge is to be used for cutting purposes, then it is also desirable to fabricate such an edge on a highly wear resistant material. Single crystal $Al_2O_3$ was chosen as one material on which to create a very sharp edge for the following reasons. It is chemically homogenous even on an atomic scale, and usually demonstrates a high degree of crystallographic perfection; i.e., it has low crystalline defect densities. As a single crystal it is intrinsically anisotropic. Its hardness and wear resistance is second only to diamond. It is significantly less expensive than diamond for similar size single crystals.

The choice of an etchant for the production of a sharp edge on a substrate of a specific material is complicated. Using etching techniques to produce a sharp edge which blends smoothly into a sharp point requires additional considerations beyond those to create a sharp edge. In order to simplify the development, the criteria for the production of an edge will be considered first.

Figure 1:
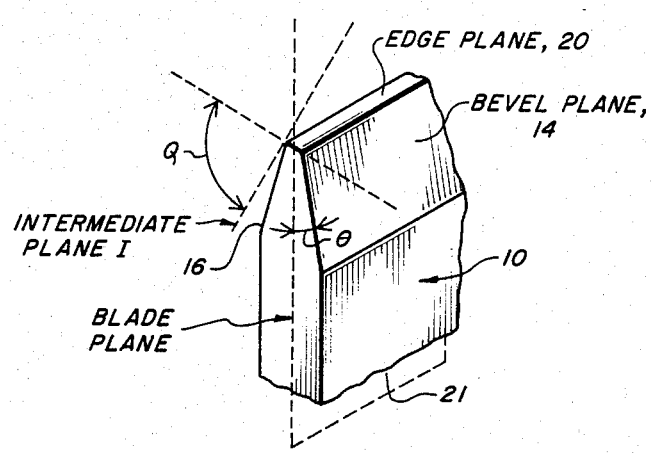
FIG. 1 is a diagrammatic illustration of a double beveled blank illustrating the blade plane, the bevel plane and the edge plane along with bevel angle $\theta$ and an intermediate plane, I, angle $\Phi$.

The following discussion applies to the production of an edge formed by two symmetric preformed bevels as shown in FIG. 1. Here a blank 10 is shown having bevels 14 and 16 with the bevel planes as indicated. The blank is provided with a flat portion 20 which initially defines the edge plane. An intermediate plane I is defined by $\Phi$ as shown. Note that the bevel angle is illustrated by the angle $\theta$. Note the blade plane is defined as plane 21 of the blank.

This type of edge is used on conventional razor blades or scalpels. Analogous reasoning can be used to establish the criteria for the production of edges in asymmetric cases such as an edge produced by a single bevel. During the sharpening process, the edge plane will be narrowed and the curvature of the blade in the region of the edge must be taken into account. For a curved edge region the edge plane will be defined as the tangent plane 22 to the blade which makes equal angles $\alpha$, $\alpha'$ with the two bevel planes 24 and 26, as shown in FIG. 2.

Figure 2:
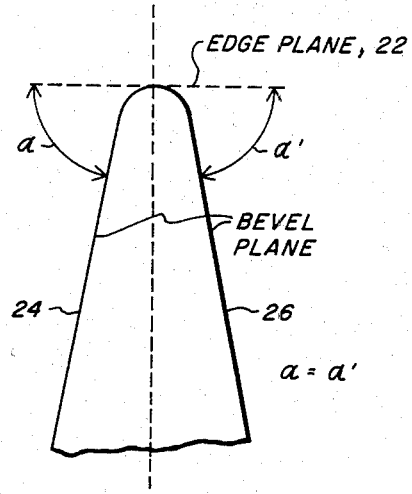
FIG. 2 is a schematic diagram defining edge radius and edge plane for a double-beveled blank.

Also shown in FIG. 2 is the parameter, r, which is defined as the average radius of curvature of the edge surface in making the transition from one bevel to the other. This parameter serves as a convenient measure of the edge sharpness and is referred to as the radius of curvature of the edge. The smaller the radius of curvature the sharper the edge.

In order to initiate this discussion it is necessary to define the terms etchant and chemical polish. An etchant is a liquid or gaseous medium which chemically removes material from the surface of an object. A chemical polish is an etchant which has an added propensity for simultaneously smoothing the surface features of the object. The rate of etching by a chemical polish or etchant will be defined as the velocity of the material-etchant interface perpendicular to the interface surface regardless of the atomic mechanism by which it occurs.

In choosing an etchant to create a sharp, straight edge, on a single crystal substrate, it is highly desirable, but not necessary, to have the following properties in the etchant-material system. At least for certain crystallographic orientations the etchant should act as a chemical polish, and not preferentially attack crystalline defects such as dislocations, twins, stacking faults, etc. The etchant should have a marked propensity for maintaining planarity in the etching of macroscopically flat surface with certain crystallographic orientations. The etchant should not degrade surface or subsurface properties of the material by, for instance, changing the chemical nature of the surface region. The etchant should not leave behind surface residues. The etch rates should be anisotropic with respect to crystallographic direction.

In order to achieve maximum blade sharpness and low blade drag with chemically polished bevel surfaces, in one embodiment, a 1:1 solution of concentrated $H_2SO_4$ and 85% concentrated $H_3PO_4$ was initially chosen as the etchant for $Al_2O_3$ because it has all of the properties listed above. It has been found that the ratio of the acids can be varied considerably and almost identical results can be achieved.

Referring to FIG. 1, blank 10 is first formed into a general blade shape by conventional procedures such as grinding and/or lapping. In this forming process the crystallographic orientation of the material must be carefully controlled. In order to produce a sharp, straight edge by etching and to produce a final blade edge configuration which is geometrically similar to the initially formed blade it is necessary that the bevel planes which form the edge should be chemically polished in the etchant and remain planar. This produces smooth side walls which form the edge and it is required in order to maintain a straight edge. The etch rates for the bevels which form the edge are made identical in order to maintain initial blade geometry. This is true if the bevel planes are crystallographically equivalent planes with respect to etching. The etch rate for the bevel planes, $V_B$, are made to satisfy the following inequality with respect to the edge plane etch rate, $V_E$. and the bevel angle, $\theta$, which is defined in FIG. 1.

$$V_B > V_E \frac{\sin \theta}{\cos^2 \theta}$$

If this inequality is not obtained, the edge plane will enlarge during etching and the edge will become duller, e.g., the edge radius of curvature will increase. If the inequality is obtained, the etch rate of the bevel planes is sufficiently rapid to decrease the size of the edge plane during the simultaneous etching of the bevel and edge planes.

It is desirable but not a requirement, to have the edge plane chemically polished in the etching process. For situations where both the edge plane and the bevel planes are chemically polished, the following criteria must be met in addition to the above criteria.

Let $\overline{\alpha}$ define the crystallographic direction which is simultaneously parallel to both the bevel and edge planes. Now consider a plane, I, which is intermediate in orientation between a bevel plane and the edge plane and which is also parallel to $\overline{\alpha}$ as shown in FIG. 1. Let $\Phi$ be defined as the angle between the edge plane and the intermediate plane I. Let $V_I$ be the etch velocity of plane I. Then $V_I$ must satisfy the following criteria.

$$V_I < \frac{\left[\left(\frac{V_B}{\cos \theta} - V_E \tan \theta\right)^2 + (V_E)^2\right]^{\frac{1}{2}}}{\cos \beta}$$

where $\beta = \phi - \tan^{-1}\left(\frac{V_E}{\frac{V_B}{\cos \theta} - V_E \tan \theta}\right)$ If this criteria is not met the angle of the bevels, $\theta$, will not be maintained in the region of the edge during etching. In particular the intermediate plane, I, which most greatly violates the above inequality will form new bevel planes in the neighborhood of the edge.

For the specific case of $Al_2O_3$ in the etchant defined above, in one embodiment, the following blade geometry and crystallographic orientation were used and all of the above criteria were met. The bevel angle $\theta$ was chosen to be 13°, consistent with the conventional blade technology. The plane of the blade was chosen to be the (0,0,0,1) plane. The edge plane was chosen to be a (1,1,2,0) plane. Thus, the bevel planes are the (1,1,$\overline{2}$,12) and (1,1,$\overline{2}$,$\overline{12}$) planes. It is a finding of this invention that if the blade plane is the (0,0,0,1) plane, that all the above requirements are met utilizing the above etchant.

With this blade edge geometry and crystallographic orientation defined above, edges with a radius of curvature less than 100 Å have been produced.

If the above criteria are met then the etching process will produce a sharpening of the edge, and bevel geometry will be maintained. By sharpening it is meant that the size of the edge plane will reduce during etching. As the edge plane narrows to very small spatial dimension, the average radius of curvature of the edge region must decrease in making the transition from one bevel plane to the other. As the bevel planes approach each other, the edge can no longer be treated as planar. The decreasing radius of curvature of this region must be taken into account. In particular the region of the edge will experience an increase in the etch rate due to surface energy effects. The smaller the radius of curvature of the edge, the faster the etch rate. This is a manifestation of the Gibbs-Thompson surface energy effect. Let the etch rate for the tangent plane to the edge region which is parallel to the previous edge plane be defined as $V_E'$. The edge will continue to narrow until such time as a steady state condition results. A steady state condition will result when $V_E'$ becomes sufficiently large that $$V_E' = \frac{V_B}{\sin \theta}$$

When this velocity limit is reached, the edge no longer changes geometry, but recedes with a constant radius of curvature.

Figure 3:
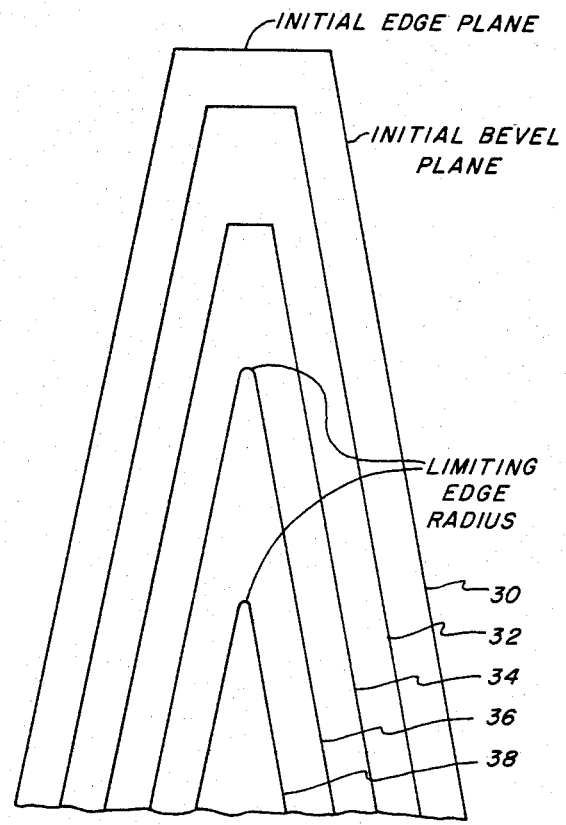
FIG. 3 is a diagrammatic illustration of the production of an edge with an etching process with the figure showing the evolution of the edge geometry and etch rates as a steady state etch rate and steady state edge geometry is produced.

This limiting process is illustrated in FIG. 3. FIG. 3 shows a time sequence of bevel and edge profiles 30–38 during the etching process. The time increment between each profile is the same. Thus, the incremental change in bevel position is constant throughout the sequence, i.e., the perpendicular distance between bevel profiles is constant. This result obtains because of constant bevel etch velocities, $V_B$. As the blade plane narrows in the sharpening process, the constant bevel etch velocity constraint requires that the edge etch velocity increase substantially. This geometrical result can be visualized in FIG. 3 by recognizing that the incremental distance traveled by the edge in the time sequence increases. The required increase in edge plane etch velocity can only be accommodated by a decrease in the radius of curvature of the edge region producing an increased etch rate.

The edge produced is extremely uniform in thickness because of the limiting process. Moreover, the edge thickness can be controlled by choosing $\theta$ and/or the ratio $V_B/V_E$. Since $V_E$ and $V_B$ will in general have different temperature dependencies, it is also in principle possible to control the steady state edge thickness by controlling temperature.

In order to achieve maximum sharpness, the crystallographic orientation defined above was chosen to make the ratio $V_B/V_E$ as large as possible and still meet other requirements. $V_B/V_E$ is approximately equal to 20 at 285° C. With a bevel angle, $\theta$, of 13°, the steady state edge velocity, $V_E'$ increases approximately 100 fold to 4.5 times the bevel etch rate.

The edges produced are extremely straight and uniform in thickness throughout their entire length. This is due to the fact that the edge formation is controlled by thermodynamic properties of the edge-etchant system and not by mechanical means as in other forming techniques. It is of importance to note that the process described is relatively insensitive to initial edge roughness. In fact, if small chips are broken from an edge which has already been formed by etching, a perfect edge can be reformed by further etching.

Care must be taken in removing the blades from the etchant and cooling to room temperature. The $Al_2O_3$ is very subject to thermal shock and thermally quenching the blades will produce mechanically weak edges which deteriorate quickly when used in cutting procedures.

Figure 4:
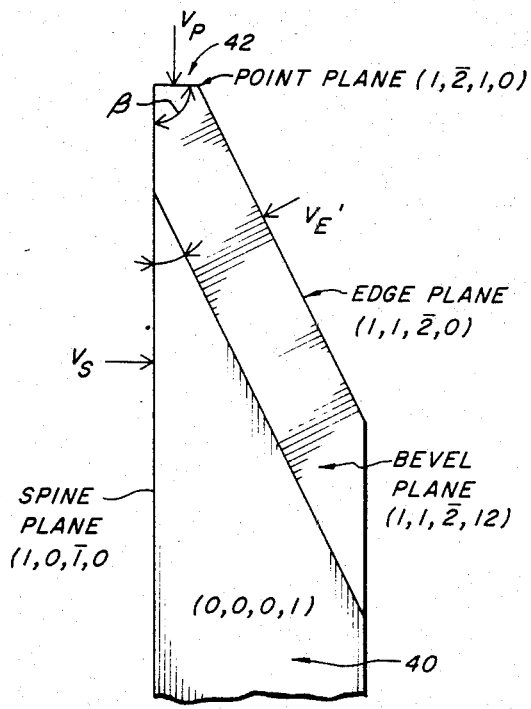
FIG. 4 is a diagrammatic illustration of the scalpel blank illustrating a typical double edge blade geometry and defining the edge plane, the bevel plane, the point plane and the etch rates associated with those planes.

FIG. 4 shows a side view of a scalpel blade 40. The schematic drawing shows that the point 42 is not well formed. As shown, point 42 is blunted by the existence of a point plane which is perpendicular to the blade plane and which makes an angle, $\beta$, with the spine plane. A configuration such as this is often encountered after the initial mechanical forming of a blade. For $Al_2O_3$ and one crystallographic orientation the bevel plane, edge plane, point plane, and spine plane as noted.

If the point etch rate, $V_p$, is too large compared to the edge etch rate $V_E$, and the spine etch rate, $V_S$, the point will blunt the cutting edge in the region near the point. In the configuration shown, the edge will not blunt in this mode if $$V_E' + \frac{V_S}{\cos \beta} \sin(\beta - \alpha) \geq V_p \cos(\beta - \alpha)$$

If the crystallographic orientation is chosen such that the etch rate, $V_B$, for the bevel planes is a maximum or near maximum for the etchant-crystal system, then the steady state value of $V'_E$ will be very large, and this mode of blunting will be prevented. The rapid motion of the edge will quickly close off the point plane.

This strategy was carried out with $Al_2O_3$. In one embodiment, the edge plane was chosen as the (1,1,2,0) plane. The bevel planes (1,1,2,12) and (1,1,2,12) etch rapidly but are not, however, the most rapidly etching planes. Nevertheless the blunting mode described above was avoided. FIG. 5 shows the pre-etch geometry of a blank 10 with an indication that the blade plane, e.g., surface 50, is the (0,0,0,1) crystallographic plane. The surface 50 is beveled at 52 as illustrated. FIGS. 6 and 6A show the geometry of the points which have been produced in $Al_2O_3$ with the edge plane being (1,1,2,0).

As can be seen in FIG. 6, the etching procedure produces a beveling 60 of the sides of the spine 62 of the blade 64. The beveling is symmetric because of crystal symmetry. This etching mode thus produced a double edge configuration at the blade point 66. The edge produced by the original bevels, edge 68, runs all the way to the point. The bevels 60 on the sides of spine 62 also produce an edge 70 from the point back a short distance along spine 62. This geometry has a strengthening effect on the blade point. It also enhances the plunging characteristics of the blade.

At lower etching temperatures ($\sim$240° C.) spine bevels do not chemically polish. However at higher temperatures there is some preliminary indication that the bevels will chemically polish.

The feasibility of producing scalpels with different crystallographic orientations have been examined. Referring now to FIG. 7, the blade plane was chosen as before to be the (0,0,0,1) plane. The edge plane was chosen to be the (1,0,1,0) plane and 13° bevel angles and a 30° point angle were maintained. Here the tip of the blade is shown in which the blade 80 has a bevel 82, a point 84, and spine bevels 86. Here no spine edge is produced. It is thus possible to successfully produce scalpels with this crystallographic orientation as well. However, some differences in etching behavior were noted. Although the bevel planes are in general chemically polished, minor etch pitting was seen at sites where dislocations intersected the bevel plane. The pitting was not found with the previous orientation. Additionally the point configuration changed significantly as shown in FIG. 7. The beveling of the spine sides by etching was again apparent in the FIG. 7 configuration but because of the difference in point etching, the spine bevels actually form the edge in the region of the point. At the etching temperatures used ($\sim$260° C.) the spine bevels did not chemically polish, so that a microscopically straight edge was not produced in the region of the point. Despite these drawbacks, the results of surgical testing showed no significant difference in performance between the two blade configurations.

Figure 8:
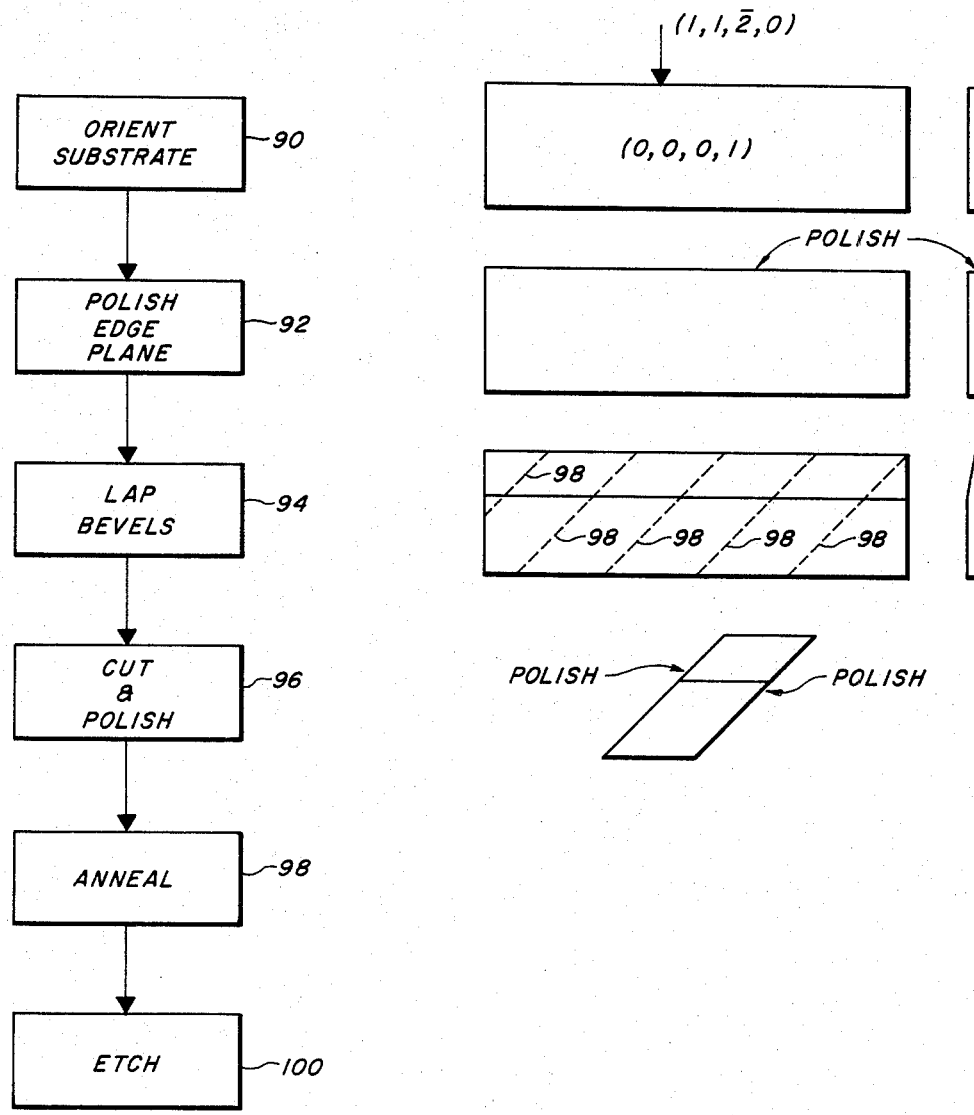
FIG. 8 is a diagram illustrating the processing steps utilized in the formation of a cutting implement from a single crystalline substrate material.

FIG. 8 illustrates one method for producing surgical scalpel blades. In an orientation step 90, the substrate is initially cut from a large single crystal with the orientation such as that shown to the right in FIG. 8. The side of the substrate where the bevels are to be formed is then mechanically polished in a step 92 to reduce the near-surface damage due to the cutting process. The preliminary bevels are then lapped in a step 94. The scalpel blank is then cut in a step 96 along dotted lines 98 from the substrate and the sides of the blank bordering the cuts are then mechanically polished in this step to reduce near-surface damage on these surfaces and to shape a preliminary point. The blank is then annealed in step 98 at elevated temperatures to further reduce near-surface damage. The blade is finally etched in a step 100 to produce the sharpened scalpel.

Having above indicated a preferred embodiment of the present invention, it will occur to those skilled in the art that modifications and alternatives can be practiced within the spirit of the invention. It is accordingly intended to define the scope of the invention only as indicated in the following claims.

What is claimed is:

1. A method of fabricating a cutting instrument from single crystal material comprising the steps of:
   providing a blank of single crystal aluminum oxide material having bevel surfaces which provide a preliminary cutting instrument edge, said blank oriented such that the (0001) plane is parallel to the planar bisector of the angle formed by the bevel surfaces of the blank which meet at the edge, the c-axis being perpendicular to said plane; and
   simultaneously etching and chemically polishing the blank to form the cutting instrument edge, said etchant acting as a chemical polish for the bevels forming said cutting instrument edge, said cutting instrument edge being perpendicular to said c-axis.

2. The method of claim 1 wherein the etchant used for etching the blank is a mixture of sulfuric acid and phosphoric acid.

3. The method of claim 1 wherein said preliminary edge defines an edge plane and wherein said edge plane is parallel to one of the planes of the form (1,1,2,0).

4. The method of claim 1 wherein said preliminary edge defines an edge plane and wherein said edge plane is parallel to one of the planes of the form (1,0,1,0,).

5. The method of claim 1 further comprising:
   selecting a combination of crystallographic orientation of said preliminary edge, the crystallographic orientations of said surfaces which provide said preliminary edge, and at least one chemical etchant, such that in said etching and polishing step the surfaces which provide said preliminary edge are etched at a rate greater than the rate of etching of said preliminary edge.

6. The method of claim 5 wherein the crystallographic orientation of said preliminary edge, the crystallographic orientations of said surfaces which provide said preliminary edge, and said chemical etchant are selected such that the ratio of the rate of etching of said edge-providing surfaces to the rate of etching of said preliminary edge is a maximum.

7. The method of claim 5 wherein in the step of simultaneously etching and chemically polishing said blank, the action of said etchant on the surfaces which provide said preliminary edge produces a narrowing of said preliminary edge and ultimately forms a sharp edge having a maximum radius of curvature of 100 Å.

8. The method of claim 1 wherein said single-crystal aluminum oxide material is ruby or sapphire.

* * * * *

UNITED STATES PATENT AND TRADEMARK OFFICE
CERTIFICATE OF CORRECTION

PATENT NO. : 4,534,827            Page 1 of 2
DATED      : August 13, 1985
INVENTOR(S): Donald W. Henderson It is certified that error appears in the above—identified patent and that said Letters Patent is hereby corrected as shown below:

In the Drawings

Fig. 1      "Q" should read --Φ--

Fig. 2      "bevel plane" should read --bevel planes--

Fig. 4      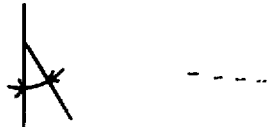   - - - -   

Fig. 6      "(1,1,2,12)" should read --(1,1,$\bar{2}$,12)--

Fig. 6      "(1,1,2,0)" should read --(1,1,$\bar{2}$,0)--

Fig. 7      "(1,0,1,0)" should read --(1,0,$\bar{1}$,0)--

Fig. 7      "(1,0,1,12)" should read --(1,0,$\bar{1}$,12)--

Column 4, line 51,  "(2,0,2,1)" should read --(2,0,$\bar{2}$,1)--

Column 5, line 38.  "(1,0,$\overline{10}$)" should read --(1,0,$\bar{1}$,0)--

Column 6, line 1,   "rounding" should read --rounded--

Column 7, line 3,   "(1,0,1,0)" should read --(1,0,$\bar{1}$,0)-- line 63,  "a the" should read --the--

Column 8, line 9,   "neccessary" should read --necessary-- lines 18-19  "homog- enous" should read --homo- geneous--

UNITED STATES PATENT AND TRADEMARK OFFICE
CERTIFICATE OF CORRECTION

PATENT NO. : 4,534,827

DATED : August 13, 1985

INVENTOR(S) : Donald W. Henderson

It is certified that error appears in the above—identified patent and that said Letters Patent is hereby corrected as shown below:

Column 9, line 43, "are" should read --is--
line 44, "$V_E.$" should read --$V_E,$--

Column 10, line 26, "(1,1,2,0)" should read --(1,1,$\bar{2}$,0)--

Column 11, line 65, "(1,1,2,0)" should read --(1,1,$\bar{2}$,0)--
line 66 (first) "(1,1,2,12)" should read --(1,1,$\bar{2}$,12)--
line 66 (second) "(1,1,2,12)" should read --(1,1,$\bar{2}$,$\overline{12}$)--

Column 12, line 6, "(1,1,2,0)." should read --(1,1,$\bar{2}$,0).--
line 18, "(~240° C.)" should read --(~24$\underline{0}$°C)--
line 26, "(1,0,1,0)" should read --(1,0,$\bar{1}$,0)--
line 35, "The" should read --This--
line 42, "(~260° C.)" should read --(~260°C)--

Column 13, line 11, "(0001)" should read --(0,0,0,1)--
line 28, "(1,1,2,0)" should read --(1,1,$\bar{2}$,0)--

Column 14, line 3, "(1,0,1,0)" should read --(1,0,$\bar{1}$,0)--

Signed and Sealed this

Twenty-eighth Day of January 1986

[SEAL]

Attest:

DONALD J. QUIGG

Attesting Officer    Commissioner of Patents and Trademarks